(12) United States Patent
Arnaud et al.

(10) Patent No.: US 6,491,927 B1
(45) Date of Patent: Dec. 10, 2002

(54) TOPICAL COMPOSITION COMPRISING A BRANCHED $C_{24}$ TO $C_{28}$ FATTY ALCOHOL OR ACID ESTER

(75) Inventors: Pascal Arnaud, L'Hay les Roses (FR); Véronique Jacques, Bourg la Reine (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/280,446

(22) Filed: Mar. 30, 1999

(30) Foreign Application Priority Data

Mar. 31, 1998 (FR) ............................................. 98 03979

(51) Int. Cl.⁷ ............................ A61K 6/00; A61K 7/00; A61K 7/04
(52) U.S. Cl. ........................ 424/401; 424/61; 424/70.1; 424/78.03
(58) Field of Search ............................ 424/78.03, 70.1, 424/401, 61

(56) References Cited

U.S. PATENT DOCUMENTS

| | | | | |
|---|---|---|---|---|
| 4,767,625 A | * | 8/1988 | Mitsuno et al. | |
| 5,585,104 A | * | 12/1996 | Ha et al. | |
| 5,603,940 A | * | 2/1997 | Candau et al. | |
| 5,639,791 A | | 6/1997 | O'Lenick, Jr. | |
| 5,711,939 A | | 1/1998 | Brunke et al. | |
| 5,830,486 A | * | 11/1998 | Nanba et al. | |
| 5,932,197 A | * | 8/1999 | Arnaud | 424/64 |
| 6,322,800 B1 | * | 11/2001 | Philippe et al. | 424/401 |

FOREIGN PATENT DOCUMENTS

| | | |
|---|---|---|
| DE | 2 339 149 | 2/1975 |
| DE | 19 516 702 | 11/1996 |
| EP | 0 550 779 | 7/1993 |
| EP | 0 596 284 | 5/1994 |
| EP | 0 667 146 | 8/1995 |
| EP | 0 792 633 | 9/1997 |
| WO | WO 93/08840 | 5/1993 |
| WO | WO 98/22085 | 5/1998 |

OTHER PUBLICATIONS

Hawley's Condensed Chemical Dictionary (John Wiley & Sons, Inc. 1997) definition of ester.*
Patent Abstracts of Japan, vol. 017, No. 391 (JP 05 070320).
Patent Abstracts of Japan, vol. 011, No. 361 (JP 62 132807).
English language Derwent Abstract of DE 2 339 149.
English language Derwent Abstract of DE 19 516 702.
English language Derwent Abstract of EP 0 550 779.
English language Derwent Abstract of EP 0 596 284.
English language Derwent Abstract of EP 0 667 146.
English language Derwent Abstract of EP 0 792 633.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

The invention relates to a topical composition and in particular a cosmetic composition comprising a saturated and branched $C_{24}$ to $C_{28}$ fatty alcohol or fatty acid ester, in particular in the form of an oil at room temperature and of high molecular weight. This composition is non-greasy and glossy and is intended in particular for caring for, treating or making up the skin, both of the human body and face, lips and superficial body growths, such as the hair, eyelashes, eyebrows or nails.

43 Claims, No Drawings

TOPICAL COMPOSITION COMPRISING A BRANCHED $C_{24}$ TO $C_{28}$ FATTY ALCOHOL OR ACID ESTER

The present invention relates to a cosmetic or dermatological topical composition comprising an ester, preferably of high molecular mass, exhibiting improved sensory properties. This ester is a saturated and branched $C_{24}$–$C_{28}$ fatty alcohol or acid ester. Another subject-matter of the invention is the use of this ester in a topical composition intended in particular for caring for, treating or making up the skin, both of the human face and body, lips and keratinous fibres or superficial body growths, such as the hair, eyelashes, eyebrows or nails.

The use is known, in the formulation of cosmetic and dermatological products, of oils with a carbon number of greater than 50 for the purpose of increasing, for example, the gloss of a lipstick, the cohesion and the adhesion of a powder, or the film-forming nature and the emollience of a product for caring for or treating the skin.

From this viewpoint, the formulator has available several types of starting materials, such as:

oily polymers, such as polybutenes, which however can exhibit the disadvantage of being very sticky, oils of plant origin which are generally oxidizable, which can result in a detrimental change in the cosmetic or dermatological properties of the product, and which also can display a very greasy and sometimes sticky nature on application, synthetic liquid esters with high molecular masses, such as pentaerythrityl tetra[isostearate] ($C_{77}$), triisoarachidyl citrate ($C_{66}$), glyceryl tri[isostearate] ($C_{57}$) or octyldodecyl stearoylstearate ($C_{56}$), but which can exhibit the disadvantages of lack of slip on application and of a sticky feel for the esters with the highest molecular masses.

The subject-matter of the present invention is specifically the use of a novel saturated and branched $C_{24}$ to $C_{28}$ fatty alcohol or acid ester in a cosmetic composition or for the preparation of a cosmetic or dermatological composition which can overcome these disadvantages.

The inventors have unexpectedly found that specific esters, composed of saturated and branched $C_{24}$ to $C_{28}$ fatty alcohols or fatty acids, do not exhibit the abovementioned disadvantages in so far as, despite a high carbon number, they possessed very good sensory properties, in particular in terms of slip during application and of absence of stickiness of the film deposited on the skin, superficial body growths or mucous membranes, such as the lips.

No one until now has disclosed or suggested the use of these esters in a composition for topical application for the purpose of contributing, according to the specific application envisaged, emollience, a film-forming nature, gloss, cohesion and/or adhesion to pulverulent compounds, without, however, contributing a sticky, greasy feel to it, and while improving its spreading and slip properties.

More specifically, the subject-matter of the invention is a topical composition comprising at least one fatty phase, characterized in that this fatty phase comprises at least one saturated and branched fatty alcohol or fatty acid ester, the carbon-comprising chain of the fatty alcohol or acid being saturated and branched and comprising 24 to 28 carbon atoms.

Another subject-matter of the invention is the use of a fatty alcohol or fatty acid ester, the carbon-comprising chain of the acid or of the alcohol of which is saturated and branched and comprises 24 to 28 carbon atoms, in a cosmetic composition or for the preparation of a dermatological composition which is non-sticky, non-greasy and/or glossy when it is applied to the skin, the lips and/or superficial body growths of a human being.

Another subject-matter of the invention is the use of a fatty alcohol or fatty acid ester, the carbon-comprising chain of the acid or of the alcohol of which is saturated and branched and comprises 24 to 28 carbon atoms, in a cosmetic composition or for the preparation of a dermatological composition in order to confer on it an emollient and/or film-forming and/or cohesive and adhesive nature when the composition is in pulverulent form.

The word ester, according to the invention, means a monoester or a polyester, including, e.g., a diester or a triester. Preferably, the polyester comprises at least two branched $C_{24}$ to $C_{28}$ chains. The word branched means at least one pendant hydrocarbon-comprising chain comprising in particular from 1 to 14 carbon atoms. Preferably, the pendant chain includes at least four carbon atoms and more preferably, two carbon atoms less than the principal chain. According to the invention, the ester is preferably a polyester, i.e., at least a diester.

The ester of the invention therefore comprises a saturated $C_{24}$ to $C_{28}$ fatty acid or fatty alcohol residue, in particular of the Guerbet fatty acid or fatty alcohol type respectively.

The ester of the composition of the invention is preferably an ester which is liquid at room temperature (20–25° C.) and which exhibits a high molecular weight, that is to say having a carbon number of greater than 50 and in particular of greater than 70. The advantage of a liquid product, in comparison with a product which is pasty or solid at room temperature, lies in the greater number of its applications and its ease of use. Furthermore, the fact that this ester exhibits a high molecular weight makes it possible to obtain a film-forming composition which is persistent with regard to water, which is much desired for protection products, in particular sun protection products. In addition, this ester can provide a glossy film, which is desired by consumers for certain make-up products, such as nail varnishes and lipsticks. It exhibits, inter alia, a refractive index of greater than 1.45 at 20° C. and an iodine number $\leq 4$.

This ester, despite its high molecular weight, is neither greasy nor heavy nor sticky and confers notable comfort properties on a composition comprising it. This ester is a "cosmetic" oil and not a surfactant.

The ester according to the invention is advantageously a liquid, branched $C_{24}$–$C_{28}$ fatty acid, such as 2-decyltetradecanoic acid, ester and more especially a polyol, such as glycerol, ester which can be a mono-, di- or triglyceride. This ester is preferably a branched $C_{24}$–$C_{28}$ triglyceride of the Guerbet type and in particular a $C_{24}$ acid, such as 2-decyltetradecanoic acid, triglyceride. Preferably, the polyol is not an ose. Further, the ester is advantageously insoluble in a mixture of water and alcohol.

This triglyceride is, for example, glyceryl tri(2-decyltetradecanoate) sold under the reference DUB TGI 24 by the Company Stéarinerie Dubois. This ester exhibits a saponification number of 140 to 150, a refractive index >1.45 and in particular ranging from 1.454 to 1.459 at 20° C., an iodine number $\leq 4$, a hydroxyl number $\leq 30$ and an acid number $\leq 10$. Its carbon number is 75.

Use may also be made of $C_{24}$ fatty acid esters of pentaerythritol, such as pentaerythrityl tetra(2-decyltetradecanoate) (comprising 101 carbon atoms) sold under the reference DUB PTI 24 by the Company Stéarinerie Dubois.

When the alcohol used in combination with the branched $C_{24}$ to $C_{28}$ fatty acid is a polyol, the esterification can be partial (and can concern 1, 2, 3 or more OH groups, depending on the alcohol used) or can be total.

Mention may be made, as ester of the invention comprising a fatty alcohol residue with a saturated and branched $C_{24}$ to $C_{28}$ chain, of di(decyltetradecyl) dimerates (comprising 84 carbon atoms), such as that sold under the reference DUB DI 24D by the Company Stéarinerie Dubois, or decyltetradecyl neopentanoate (comprising 29 carbon atoms) or decyltetradecyl isostearate, sold by the Company Condea under the reference Isofol Ester 2482 (comprising 42 carbon atoms). The dimerates are diacids, generally of a $C_6$ to $C_{24}$ acid, such as oleic acid, linoleic acid, linolenic acid, and the like.

The ester according to the invention can represent from 0.1 to 99.9% of the weight of the composition, preferably from 1 to 99% and better still from 5 to 90% and can generally be present in an amount sufficient to confer non-greasy, non-sticky, slip and/or gloss properties on the composition.

The sensory properties of the ester according to the invention were demonstrated through a test carried out on a panel of five people using a protocol disclosed in the document EP-A-550779 of the Company Nestlé, the disclosure of which is specifically incorporated by reference herein.

The applications of the ester of the invention are numerous and relate to all cosmetic and dermatological products.

The products of the invention can be provided in the form of solid, pasty or liquid compositions which are anhydrous or in the form of emulsions.

Thus, the composition of the invention can be provided in all the dosage forms normally used for topical application, including pharmaceutical dosage forms, and in particular in the form of an oily gel, of an oil-in-water or water-in-oil emulsion, or of a dispersion of oil in water by virtue of vesicles, the vesicles being situated at the oil/water interface. This composition can have the appearance of a cream, of an ointment, of a supple paste, of a salve, of a cast or moulded solid, in particular a stick or dish, or of a compacted solid.

More specifically, the subject-matter of the invention is a lip product comprising a liquid fatty phase comprising at least one ester as defined above.

The composition according to the invention can advantageously be used for treating, making-up or caring for the skin and/or mucous membranes, depending on the nature of the active principles used. In particular, the composition of the invention can be a lipstick stick or a lip gloss which can be used by itself or for application to a lipstick film, in particular in order to enhance its gloss (topcoat). It can also constitute a liquid or solid foundation, a product for combatting rings under the eyes or circles around the eyes, an eyeliner, a mascara, a face powder, an eyeshadow, a nail varnish, a free powder, a product for making up the body or alternatively a sun protection product or a product for caring for or cleansing the skin, such as scrubs. These compositions can additionally comprise cosmetic or dermatological active principles for the purpose, in particular, of contributing a care or treating aspect to the composition. Thus, the composition can comprise vitamins and other lipophilic active principles (lanolin, UVA screening agent) or hydrophilic active principles (moisturizers, such as glycerol).

The composition of the invention can additionally comprise any other ingredient conventionally used in the fields under consideration. In particular, it can comprise a particulate filler which can represent from 0 to 35% of the total weight of the composition, preferably from 0.5 to 20%, and which can comprise pigments and/or pearlescent agents and/or fillers commonly used in cosmetic or dermatological compositions. This filler can result in a coloured, white or colourless composition.

Pigments should be understood as meaning inorganic or organic, white or coloured particles which are insoluble in the liquid fatty phase and which are intended to colour and/or opacify the composition. Fillers should be understood as meaning inorganic or synthetic, lamellar or non-lamellar, colourless or white particles. Pearlescent agents should be understood as meaning iridescent particles, in particular produced by certain molluscs in their shells or else synthesized. These fillers and pearlescent agents are used in particular to modify the texture of the composition.

The pigments can be present in the composition in a proportion ranging from 0.05 to 25% of the weight of the final composition and preferably in a proportion from 2 to 15%. Mention may be made, as inorganic pigments which can be used in the invention, of titanium, zirconium or cerium oxides as well as zinc, iron or chromium oxides and ferric blue. Mention may be made, among organic pigments which can be used in the invention, of carbon black and barium, strontium, calcium (DC Red No.7) or aluminium lakes.

The pearlescent agents can be present in the composition in a proportion ranging from 0 to 20% of the total weight of the composition, preferably at a high level of the order of 1 to 15%. Mention may be made, among the pearlescent agents which can be used in the invention, of mica covered with titanium oxide, with iron oxide, with natural pigment or with bismuth oxychloride, such as coloured titanium oxide-coated mica.

The fillers can be present in a proportion ranging from 0 to 35% of the total weight of the composition, preferably from 0.5 to 15%. Mention may in particular be made of talc, mica, kaolin, nylon powder (in particular Orgasol), polyethylene powder, Teflon, starch, boron nitride, microspheres of copolymers, such as Expancel (Nobel Industrie) or polytrap (Dow Corning), and silicone resin microbeads (Tospearl from Toshiba, for example).

In addition, the fatty phase advantageously comprises one or more other fatty substances and in particular waxes, gums and oils.

The waxes can be hydrocarbon-comprising, fluorinated and/or silicone waxes and can be of plant, mineral, animal and/or synthetic origin. In particular, they exhibit a melting temperature of greater than 25° C. and better still of greater than 45° C.

Mention may be made, as wax which can be used in the invention, of lanolin, which may or may not be oxypropylenated and which may or may not be acetylated, beeswax, carnauba wax, candelilla wax, paraffin, lignite or microcrystalline waxes, ceresin or ozokerite; synthetic waxes, such as polyethylene waxes and Fischer-Tropsch waxes, or alternatively esters, such as octacosanyl stearate, or silicone waxes, such as alkyl- or alkoxydimethicones having an alkyl or alkoxy chain comprising 16 to 45 carbon atoms.

The nature and the amount of the gums or waxes depend on the desired textures and mechanical properties. By way of indication, the composition can comprise from 0 to 50% by weight of waxes with respect to the total weight of the composition and better still from 5 to 30%.

The oils can be hydrocarbon-comprising and/or silicone and/or fluorinated oils. These oils can be of animal, plant, mineral or synthetic origin. Mention may be made, as example of oil which can be used in the invention, of hydrocarbon-comprising oils of animal origin, such as perhydrosqualene; plant hydrocarbon- comprising oils, such as liquid triglycerides of fatty acids comprising 4 to 10 carbon atoms, such as triglycerides of heptanoic or octanoic acids, hydrogenated coconut triglycerides and triglycerides of caprylic/capric acids, such as those sold by the Company Stéarinerie Dubois or those sold under the names Miglyol 810, 812 and 818 by the Company Dynamit; linear or branched hydrocarbons of mineral or synthetic origin, such as liquid paraffins and their derivatives, petrolatum, polydecenes or hydrogenated polyisobutene, such as parleam; sythetic esters and ethers, in particular of fatty acids, such as oils of formula $R_1COOR_2$ in which $R_1$ represents the residue of a higher fatty acid comprising from 7 to 29 carbon atoms and $R_2$ represents a hydrocarbon-comprising chain comprising from 3 to 30 carbon atoms, such as, for example, purcellin oil, isopropyl myristate, 2-ethylhexyl palmitate, 2-octyidodecyl stearate, 2-octyldodecyl erucate or isostearyl isostearate; hydroxylated esters, such as isostearyl lactate, octyl hydroxystearate, octyidodecyl hydroxystearate, diisostearyl malate, triisocetyl citrate, or heptanoates, octanoates or decanoates of fatty alcohols; polyol esters, such as propylene glycol dioctanoate, neopentyl glycol dihepanoate, diethylene glycol diisononanoate and pentaerythritol esters; fatty alcohols having from 12 to 26 carbon atoms, such as octyldodecanol, 2-butyloctanol, 2-hexyldecanol, 2-undecylpentadecanol or oleyl alcohol; silicone oils, such as polydimethylsiloxanes (PDMS), which may or may not be volatile, which are linear or cyclic and which are liquid or pasty at room temperature; or their mixtures.

These oils can represent from 0 to 99.9% by weight with respect to the liquid fatty phase and better still from 0 to 95%.

Mention may be made, as other ingredient which can be used in the invention, of preservatives, thickeners for the aqueous or fatty phase (Bentone or silica), fragrances, surfactants, antioxidants and their mixtures. The amounts of these various ingredients are those conventionally used in the fields under consideration, for example from 0.01% to 20% of the total weight of the composition. The nature of these ingredients and their proportion should be compatible with the properties desired for the compositions of the invention. The composition can also comprise water in a proportion ranging from 0 to 95% of the total weight of the composition.

A further subject-matter of the invention is the cosmetic use of the above composition for caring for and/or making up the skin and/or mucous membranes and/or superficial body growths and more especially the lips, as well as the use of this composition for the preparation of a dermatological composition intended to treat the skin and/or mucous membranes and in particular the lips and/or superficial body growths. Another subject-matter of the invention is a process for the cosmetic and/or dermatological treatment of the skin and/or mucous membranes and in particular of the lips and/or superficial body growths which comprises applying the composition defined above to the skin and/or mucous membranes and in particular the lips and/or superficial body growths of human beings.

A further subject-matter of the invention is a process for conferring a non-sticky and/or non-greasy feel and/or glossy aspect and/or a film-forming nature on a topical composition which comprises introducing at least one ester as defined above into a cosmetic and/or dermatological medium. A further subject-matter of the invention is a cohesion and/or adhesion on a pulverulent topical composition which comprises introducing at least one ester as defined above into the composition.

The composition of the invention can be obtained by heating the various constituents to the melting temperature of the highest melting temperature constituent and then casting the molten mixture in a mould (dish or thimble). It can also be obtained by extrusion, as disclosed in Application EP-A-667,146, the disclosure of which is specifically incorporated by reference herein.

The following composition examples are given by way of illustration and without a limiting nature. The amounts are given therein as % by weight.

EXAMPLE 1

Gloss in a Pot

| | |
|---|---|
| $C_{24}$ triglyceride (DUB TGI 24) | 81% |
| Hydrophobic pyrogenic silica (Aerosil R972 from Degussa) | 9% |
| Pearlescent agent | 9.5% |
| Preservative, antioxidant | 0.5% |

Procedure: The silica is dispersed in the oil at room temperature using a Rayneri at a speed of 1000 rev/min. The pearlescent agents are added while continuing to stir and the composition is poured into pots. A very lustrous gloss is thus obtained which is easy to apply and which shows very little sign of stickiness.

EXAMPLE 2

Gloss in a Jar

| | |
|---|---|
| $C_{24}$ triglyceride (DUB TGI 24) | 34.0% |
| Lanolin oil | 40.0% |
| Octyldodecanol | 14.0% |
| Polyethylene wax | 6.0% |
| Microcrystalline wax | 3.0% |
| Pigment | 2.0% |
| Preservative, antioxidant | 0.5% |
| Fragrance | 0.5% |

Procedure: The constituents are mixed and heated to 100–105° C. After homogenizing and milling the pigments, the mixture is cast at 100° C. into appropriate jars. A very lustrous gloss is thus obtained which is not very sticky.

EXAMPLE 3

Lipstick Stick

| | |
|---|---|
| $C_{24}$ triglyceride (DUB TGI 24) | 7.0% |
| Dioctyldodecyl dilinoleate dimer | 24.0% |
| Octyldodecanol | 15.0% |
| Capric/caprylic acid triglyceride | 10.0% |
| Bentone (quaternium-18 hectorite) | 0.6% |
| Lanolin oil | 11.0% |
| Oxypropylenated (5 PO) lanolin | 5.0% |
| Acetylated lanolin | 5.0% |
| Polyethylene wax | 8.0% |
| Octacosanyl stearate | 5.0% |
| Hydrogenated coconut glycerides | 2.0% |
| Pigments | 7.0% |
| Fragrance, preservative, antioxidant | 0.4% |

Procedure: The Bentone is dispersed in a portion of the oily phase and then the remainder of the fatty phase is added and heated to 95° C. After homogenizing and milling the pigments, the mixture is cast into appropriate moulds. A lipstick stick is then obtained which exhibits good cosmetic properties with regard to application and gloss.

1st) Comparative Test a) Test

The test consists of a comparison, through a simple formula in the form of a silica gel, of the cosmetic properties of the ester of the invention (in this instance DUB TGI 24) (Composition B) with those of pentaerythrityl tetra[isostearate] (Composition A) and glyceryl tri[isostearate] (Composition C).

Pentaerythrityl tetra[isostearate] ($C_{77}$) was chosen as representing an oily ester of high molecular mass. Glyceryl tri[isostearate] ($C_{57}$) was chosen as representing an ester having a chemical structure similar to some extent but not suggestive of that of the ester of the invention.

The comparison was made from the following formulae:

| COMPOSITIONS | A | B | C |
|---|---|---|---|
| Pyrogenic silica, sold under the ref. Aerosil R972 by Degussa | 9.00% | 9.00% | 9.00% |
| Pentaerythrityl tetra[isostearate], sold under the reference Prisorine PTIS 3631 by Unichema | 90.13% | — | — |
| Ester of the invention, sold under the reference DUB TGI 24 by Stéarinerie Dubois | — | 90.13% | — |
| Glyceryl tri[isostearate], sold by Stéarinerie Dubois | — | — | 90.13% |
| Preservative | 0.40% | 0.40% | 0.40% |
| Antioxidant | 0.07% | 0.07% | 0.07% |
| Fragrance | 0.40% | 0.40% | 0.40% |

For each formula, the silica was dispersed in the oil with the Rayneri at room temperature.

b) Protocol of the Test

The test was carried out on 5 people while following the protocol disclosed in the document EP 550,779 of Nestlé. This is because this method makes it possible to numerically quantify by an index (IOF, index of feel) the various characteristics which define the feel of cosmetic products.

The IOF comprises three parameters;

The initial feel, comprising:
- a textural grade from 1 (too dry) to 5 (too greasy)
- a slipping grade from 1 (slows down too much) to 5 (slips well), the grading constituting the mean of the two grades.

The intermediate feel during the spreading, comprising:
- a spreading grade from 1 (slows down too much) to 5 (slips well),
- a sticky nature grade from 1 (too sticky) to 5 (not sticky),
- a rate of penetration grade from 1 (very slow) to 5 (rapid),
- a degree of penetration grade from 1 (non-existent) to 5 (very good), the grading constituting the mean of the four grades.

The final feel comprising:
- a grade of impression on rubbing from 1 (slows down too much) to 5 (slips well),
- a grade characterizing the residual lipid film on the skin from 1 (non-existent-dry skin) to 5 (rich - well-nourished skin), the grading being the sum of the two grades.

The IOF is expressed by the grading of the initial feel/the sum of the grading of the intermediate feel and of the grading of the final feel. The samples of products to be tested are submitted to the experimenters, who apply them successively to the inside of the forearms. The amount of product to be applied must be the same for each test, that is to say approximately 0.2 g.

c) Results of the Test

TABLE I

| COMPOSITIONS | A | B | C |
|---|---|---|---|
| Initial feel | | | |
| Textural grade | 3.60 | 3.40 | 3.70 |
| Slipping grade | 2.90 | 4.20 | 3.40 |
| Mean | 3.25 | 3.80 | 3.55 |
| Intermediate feel | | | |
| Spreading grade | 2.00 | 3.90 | 3.40 |
| Sticky nature grade | 1.50 | 3.50 | 3.20 |
| Rate of penetration grade | 2.80 | 2.50 | 1.30 |
| Degree of penetration grade | 2.60 | 2.30 | 2.00 |
| Mean | 2.23 | 3.05 | 2.48 |
| Final feel | | | |
| Rubbing grade | 2.30 | 4.10 | 3.40 |
| Residual lipid film grade | 3.00 | 3.70 | 2.80 |
| Sum | 5.30 | 7.80 | 6.20 |
| IOF | 3.25/7.53 | 3.80/10.85 | 3.55/8.68 |

The sensory properties improve as the numerator and the denominator of the IOF increase.

It clearly emerges from this test that the ester according to the invention provides improved properties with respect to those of the prior art.

Of course, the cosmetic properties of this branched $C_{24}$ fatty acid triglyceride are entirely comparable with those of the branched $C_{24}$ fatty alcohol esters comprising a similar total number of atoms.

2nd) Comparative Test

In this test, the cosmetic properties of the ester of the invention (in this instance DUB PTI 24) (Composition E) were compared with those of pentaerythrityl tetra[isostearate] (comprising 77 carbon atoms) sold under the reference Prisorine (PTIS 3631) by the company Unichema (Composition D).

The comparison was made under the same conditions as in part 1) on the following Compositions D and E. The results of this test are carried in Table II.

| COMPOSITIONS | D | E |
|---|---|---|
| Pyrogenic silica, sold under the ref. Aerosil R972 by Degussa | 9.00% | 9.00% |
| Pentaerythrityl tetra[isostearate], sold under the form PTIS 3631 | 90.13% | |
| Pentaerythrityl tetra[decyltetradecanoate] (DUB PTI24) | | 90.13% |
| Preservative | 0.40% | 0.40% |
| Antioxidant | 0.07% | 0.07% |
| Fragrance | 0.40% | 0.40% |

TABLE II

| COMPOSITIONS | D | E |
|---|---|---|
| Initial feel | | |
| Textural grade | 4.00 | 4.00 |
| Slipping grade | 2.60 | 2.60 |
| Mean | 3.30 | 3.30 |
| Intermediate feel | | |
| Spreading grade | 2.40 | 2.80 |

TABLE II-continued

| COMPOSITIONS | D | E |
|---|---|---|
| Sticky nature grade | 2.80 | 3.40 |
| Rate of penetration grade | 2.40 | 2.00 |
| Degree of penetration grade | 2.80 | 2.20 |
| Mean | 2.60 | 2.60 |
| Final feel | | |
| Rubbing grade | 2.20 | 2.80 |
| Residual lipid film grade | 3.20 | 3.80 |
| Sum | 5.40 | 6.60 |
| IOF | 3.30/8.00 | 3.30/9.20 |

It clearly emerges from Table II that the ester of the invention provides improved properties with respect to those of the ester not comprising a branched $C_{24}$–$C_{28}$ chain.

3rd) Comparative Test

In this test, the cosmetic properties of decyltetradecyl isostearate (comprising 42 carbon atoms), sold under the reference Isofol Ester 2482 by the Company Condea (Composition G), were compared with those of oleyl erucate (comprising 40 carbon atoms), sold by the company Henkel under the reference Cetiol J-600 (Composition F).

The comparison was made under the same conditions as in part 1) on Compositions F and G below. The results are carried in Table III.

| COMPOSITIONS | F | G |
|---|---|---|
| Pyrogenic silica, sold under the ref. Aerosil R972 by Degussa | 9.00% | 9.00% |
| Oleyl erucate (Cetiol J-600) | 90.13% | |
| Decyltetradecyl isostearate (Isofol Ester 2482) | | 90.13% |
| Preservative | 0.40% | 0.40% |
| Antioxidant | 0.07% | 0.07% |
| Fragrance | 0.40% | 0.40% |

TABLE III

| COMPOSITIONS | F | G |
|---|---|---|
| Initial feel | | |
| Textural grade | 3.00 | 3.80 |
| Slipping grade | 3.60 | 3.60 |
| Mean | 3.30 | 3.70 |
| Intermediate feel | | |
| Spreading grade | 3.60 | 3.40 |
| Sticky nature grade | 4.40 | 4.20 |
| Rate of penetration grade | 3.00 | 3.80 |
| Degree of penetration grade | 3.60 | 3.80 |
| Mean | 3.65 | 3.80 |
| Final feel | | |
| Rubbing grade | 3.00 | 3.00 |
| Residual lipid film grade | 2.40 | 2.80 |
| Sum | 5.40 | 5.80 |
| IOF | 3.30/9.05 | 3.70/9.60 |

Here again, the ester of the invention (branched $C_{24}$ fatty alcohol residue) provides improved properties with respect to those of the ester of the prior art (without a branched $C_{24}$ to $C_{28}$ chain).

4th) Comparative Test

In this test, the cosmetic properties of the ester according to the invention (in this instance DUB DI 24 D) (Composition I) were compared with those of a dimer of the prior art, di(octyldodecyl) dilinoleate (comprising 76 carbon atoms), sold under the reference Liquiwax DIEFA by the Company Brooks Ind. (Composition H). Compositions H and I are given below and the results of the tests are carried in Table IV.

| COMPOSITIONS | H | I |
|---|---|---|
| Pyrogenic silica, sold under the ref. Aerosil R972 by Degussa | 9.00% | 9.00% |
| Di(octyldodecyl) dilinoleate dimer (Liquiwax DIEFA) | 90.13% | |
| Di(decyltetradecyl) dimerate (DUB DI 24 D) | | 90.13% |
| Preservative | 0.40% | 0.40% |
| Antioxidant | 0.07% | 0.07% |
| Fragrance | 0.40% | 0.40% |

TABLE IV

| COMPOSITIONS | H | I |
|---|---|---|
| Initial feel | | |
| Textural grade | 4.00 | 3.80 |
| Slipping grade | 3.00 | 4.00 |
| Mean | 3.50 | 3.90 |
| Intermediate feel | | |
| Spreading grade | 2.70 | 3.60 |
| Sticky nature grade | 2.60 | 3.40 |
| Rate of penetration grade | 2.00 | 2.60 |
| Degree of penetration grade | 2.60 | 2.80 |
| Mean | 2.50 | 3.10 |
| Final feel | | |
| Rubbing grade | 2.00 | 3.40 |
| Residual lipid film grade | 3.60 | 3.60 |
| Sum | 5.60 | 7.00 |
| IOF | 3.50/8.10 | 3.90/10.10 |

Here again, the ester of the invention ($C_{24}$ fatty alcohol residue) provides improved properties with respect to those of the ester of the prior art (without a branched $C_{24}$ to $C_{28}$ chain).

What is claimed is:

1. A cosmetic or dermatological composition comprising at least one fatty phase, wherein said at least one fatty phase comprises at least one polyester chosen from fatty alcohol and fatty acid polyesters, wherein said at least one polyester comprises at least one saturated, branched $C_{24}$ to $C_{28}$ carbon atom chain, with the proviso that the at least one polyester does not comprise an ose, and wherein said at least one polyester is present in a cosmetically effective amount, said amount providing the composition with at least one property chosen from non-greasy, non-sticky, slip, and gloss.

2. A composition according to claim 1, wherein said at least one polyester comprises at least two saturated and branched $C_{24}$ to $C_{28}$ chains.

3. A composition according to claim 2, wherein said at least one polyester comprises a carbon number >50.

4. A composition according to claim 3, wherein said at least one polyester comprises a carbon number >70.

5. A composition according to claim 2, wherein said at least one polyester is chosen from branched $C_{24}$ fatty alcohol and branched $C_{24}$ fatty acid polyesters.

6. A composition according to claim 2, wherein said at least one polyester is liquid at room temperature.

7. A composition according to claim 1, wherein said at least one polyester is chosen from branched $C_{24}$ fatty acid triglycerides, branched $C_{24}$ fatty acid esters of pentaerythritol, and branched $C_{24}$ fatty alcohol esters of diacids.

8. A composition according to claim 2 wherein the refractive index of said at least one polyester is greater than 1.45 at 20° C.

9. A composition according to claim 1, wherein said at least one polyester exhibits an iodine number $\leq 4$.

10. A composition according to claim 2, wherein said at least one polyester is chosen from branched $C_{24}$ fatty acid triglycerides.

11. A composition according to claim 2, wherein said at least one polyester is the triglyceride of 2-decyltetradecanoic acid.

12. A composition according to claim 2, wherein said at least one polyester is present in an amount sufficient to confer non-greasy, non-sticky, slip and/or gloss properties to the composition.

13. A composition according to claim 2, wherein said composition is provided in the form of a product for making up and/or caring for the face or body, lips and/or superficial body growths.

14. A composition for caring for or making up the lips comprising an effective amount of at least one fatty phase, wherein said at least one fatty phase comprises at least one polyester chosen from fatty alcohol and fatty acid polyesters, wherein said at least one polyester comprises at least one saturated, branched $C_{24}$ to $C_{28}$ carbon atom chain, with the proviso that the at least one polyester does not comprise an ose, and wherein said at least one polyester is present in a cosmetically effective amount, said amount providing the composition with at least one property chosen from non-greasy, non-sticky, slip, and gloss.

15. A composition according to claim 14, wherein said at least one polyester comprises at least two saturated and branched $C_{24}$ to $C_{28}$ chains.

16. A composition according to claim 1, further comprising at least one wax, and/or at least one particulate filler, and/or at least one oil other than said at least one polyester.

17. A method for preparing a cosmetic composition or a dermatological composition which is non-sticky, non-greasy and/or glossy when it is applied to the skin, lips and/or superficial body growths of a human being comprising the step of including in said composition an effective amount of at least one fatty phase, wherein said fatty phase comprises at least one polyester chosen from fatty alcohol and fatty acid polyesters, wherein said at least one polyester comprises at least one saturated, branched $C_{24}$ to $C_{28}$ carbon atom chain, with the proviso that the polyester does not comprise an ose.

18. A method according to claim 17, wherein said at least one polyester comprises at least two saturated and branched $C_{24}$ to $C_{28}$ chains.

19. A method of conferring on a cosmetic composition or a dermatological composition an emollient and/or film-forming and/or cohesive and adhesive nature when said composition is in pulverulent form comprising the step of including in said composition, in an amount effective to achieve one or more of said purposes, at least one fatty phase, wherein said at least one fatty phase comprises at least one polyester chosen from fatty alcohol and fatty acid polyesters, wherein said at least one polyester comprises at least one saturated, branched $C_{24}$ to $C_{28}$ carbon atom chain, with the proviso that the at least one polyester does not comprise an ose.

20. A method according to claim 19, wherein said at least one polyester comprises at least two saturated and branched $C_{24}$ to $C_{28}$ chains.

21. A method according to claim 18, wherein said at least one polyester is liquid at room temperature.

22. A method according to claim 20, wherein said at least one polyester is liquid at room temperature.

23. A method according to claim 17, wherein said at least one polyester is chosen from branched $C_{24}$ fatty acid triglycerides, branched $C_{24}$ fatty acid esters of pentaerythritol, and branched $C_{24}$ fatty alcohol esters of diacids.

24. A method according to claim 19, wherein said at least one polyester is chosen from branched $C_{24}$ fatty acid triglycerides, branched $C_{24}$ fatty acid polyesters of pentaerythritol, and branched $C_{24}$ fatty alcohol polyesters of diacids.

25. A method according to claim 18, wherein said at least one polyester is chosen from branched $C_{24}$ fatty acid tryglycerides.

26. A method according to claim 20, wherein said at least one polyester is chosen from branched $C_{24}$ fatty acid tryglycerides.

27. A method according to claim 26, wherein said at least one polyester is the triglyceride of 2-decyltetradecanoic acid.

28. A method according to claim 25, wherein said at least one polyester is the triglyceride of 2-decyltetradecanoic acid.

29. A method for the cosmetic treatment of the skin and/or a mucous membrane comprising the step of applying thereto an effective amount of at least one fatty phase, wherein said fatty phase comprises at least one polyester chosen from fatty alcohol and fatty acid polyesters, wherein said at least one polyester comprises at least one saturated, branched $C_{24}$ to $C_{28}$ carbon atom chain, with the proviso that the polyester does not comprise an ose.

30. A method according to claim 29, wherein said at least one polyester comprises at least two saturated and branched $C_{24}$ to $C_{28}$ chains.

31. A method according to claim 30 wherein lips and/or superficial body growths of human beings are treated.

32. A cosmetic or dermatological composition comprising:
   at least one fatty phase, wherein said at least one fatty phase comprises at least one aliphatic polyester chosen from fatty alcohol and fatty acid polyesters, wherein said at least one aliphatic polyester comprises at least one saturated, branched $C_{24}$ to $C_{28}$ carbon atom chain, with the proviso that the at least one aliphatic polyester does not comprise an ose; and
   at least one additional component chosen from at least one wax, at least one particulate filler, and at least one oil, wherein said at least one oil is different from said at least one aliphatic polyester.

33. The cosmetic composition of claim 32, wherein said composition is a composition effective for at least one of caring for and making up lips.

34. A method for preparing the cosmetic composition according to claim 32, wherein said cosmetic composition exhibits at least one property chosen from non-sticky, non-greasy, and glossy when applied to at least one of skin and superficial body growths of a human being, said method comprising including in said composition an effective amount of said at least one fatty phase; and including in said composition said at least one additional component.

35. A method for conferring on the cosmetic composition according to claim 32 at least one property chosen from emollient, film-forming, cohesive, and adhesive when said cosmetic composition is in pulverulent form, said method comprising including in said cosmetic composition, in an amount effective to achieve said at least one property, said at least one fatty phase; and including in said composition said at least one additional component.

36. A method for cosmetically treating at least one of skin and mucous membranes, said method comprising applying to said skin and/or mucous membranes the cosmetic composition of claim 32.

37. A cosmetic or dermatological composition comprising:
- at least one fatty phase, wherein said at least one fatty phase comprises at least one polyester chosen from fatty alcohol and fatty acid polyesters, wherein said at least one polyester comprises at least one saturated, branched $C_{24}$ to $C_{28}$ carbon atom chain and is chosen from branched $C_{24}$ triglycerides, branched $C_{24}$ fatty acid esters of pentaerythritol, and branched $C_{24}$ fatty alcohol esters of diacids, with the proviso that the at least one polyester does not comprise an ose; and
- at least one additional component chosen from at least one wax, at least one particulate filler, and at least one oil, wherein said at least one oil is different from said at least one polyester.

38. The cosmetic composition of claim 37, wherein said composition is a composition effective for at least one of caring for and making up lips.

39. A method for preparing the cosmetic composition according to claim 37 wherein said cosmetic composition exhibits at least one property chosen from non-sticky, non-greasy, and glossy when applied to at least one of skin and superficial body growths of a human being, said method comprising including in said composition an effective amount of said at least one fatty phase; and including in said composition said at least one additional component.

40. A method for conferring on the cosmetic composition according to claim 37 at least one property chosen from emollient, film-forming, cohesive, and adhesive when said cosmetic composition is in pulverulent form, said method comprising including in said cosmetic composition, in an amount effective to achieve said at least one property, said at least one fatty phase; and including in said composition at least one additional component.

41. A method for cosmetically treating at least one of skin and mucous membranes, said method comprising applying to said skin and/or mucous membranes the cosmetic composition of claim 37.

42. The composition according to claim 1, wherein said composition comprises said at least one polyester in an amount by weight ranging from 0.1 to 99.9%.

43. The composition according to claim 14, wherein said composition comprises said at least one polyester in an amount by weight ranging from 0.1 to 99.9%.

* * * * *